US006303123B1

(12) United States Patent
Grimes et al.

(10) Patent No.: US 6,303,123 B1
(45) Date of Patent: *Oct. 16, 2001

(54) METHODS FOR THE TREATMENT OF HORMONE-DEPENDENT TUMORS WITH IMMUNOGENS AGAINST GONADOTROPIN RELEASING HORMONE

(75) Inventors: Stephen Grimes, Davis; Robert Scibienski, Woodland, both of CA (US)

(73) Assignee: Aphton Corporation, Woodland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/478,546

(22) Filed: Jun. 7, 1995

Related U.S. Application Data

(63) Continuation-in-part of application No. 08/188,223, filed on Jan. 27, 1994, now Pat. No. 5,688,506.

(51) Int. Cl.[7] .......................... A61K 39/00; A61K 38/00; C07K 5/00; C07K 17/00
(52) U.S. Cl. ..................................... 424/184.1; 424/185.1; 424/193.1; 424/194.1; 424/198.1; 530/850; 530/300; 530/313; 530/326; 530/327; 530/328; 530/329; 530/810; 530/827; 530/852; 530/853; 530/854; 514/2; 514/800; 930/110; 930/130
(58) Field of Search ........................... 424/184.1, 185.1, 424/193.1, 194.1, 198.1; 530/850, 300, 313, 326, 327, 328, 329, 810, 827, 852–854; 514/2, 800; 930/110, 130

(56) References Cited

U.S. PATENT DOCUMENTS

| 3,963,691 | 6/1976 | Hoffman et al. . |
| 4,201,770 | 5/1980 | Stevens ................................ 424/177 |
| 4,302,386 | 11/1981 | Stevens ........................... 260/112.5 |
| 4,384,995 | 5/1983 | Stevens ........................... 260/112.5 |
| 4,526,716 | 7/1985 | Stevens ........................... 260/112.5 |
| 4,608,251 | 8/1986 | Mia ........................................ 424/85 |
| 4,618,598 | 10/1986 | Conn . |
| 4,676,981 | 6/1987 | Silversides ........................... 424/85 |
| 4,691,006 | 9/1987 | Stevens ................................ 530/324 |
| 4,780,312 | 10/1988 | Talwar . |
| 4,795,634 | * 1/1989 | Grimes et al. . |

(List continued on next page.)

FOREIGN PATENT DOCUMENTS

| 4003944 | 8/1991 | (DE) . |
| 0323769 | 11/1988 | (EP) . |
| A20293530 | 12/1988 | (EP) . |
| 0380230 | 8/1990 | (EP) . |
| 0578293 | 1/1994 | (EP) . |
| 2593705 | 2/1986 | (FR) . |
| 2228262 | * 8/1990 | (GB) . |
| 8604243 | 7/1986 | (WO) . |
| 8606635 | 11/1986 | (WO) . |
| 8607383 | 12/1986 | (WO) . |
| 8800056 | 7/1987 | (WO) . |
| 9009799 | 9/1990 | (WO) . |
| 9102799 | 3/1991 | (WO) . |
| 9104052 | 4/1991 | (WO) . |
| 9116343 | 10/1991 | (WO) . |
| 9212247 | 7/1992 | (WO) . |
| 9212733 | 8/1992 | (WO) . |
| 9215330 | 9/1992 | (WO) . |
| 9219746 | 11/1992 | (WO) . |
| 9002187 | 2/1993 | (WO) . |
| 9302706 | 2/1993 | (WO) . |
| 9303058 | 2/1993 | (WO) . |
| 9308290 | 4/1993 | (WO) . |
| 9319781 | 10/1993 | (WO) . |
| 9400590 | 1/1994 | (WO) . |
| 9425060 | 11/1994 | (WO) . |
| WO9715316 | * 5/1997 | (WO) . |
| WO9715325 | * 5/1997 | (WO) . |

OTHER PUBLICATIONS

Sad et al, 1991, J. Reprod. Immunol. 20:189–194.*
Sad et al., 1993 Vaccine 11(11):1145–1150.*
Milovanovic et al, 1993 J. Cancer Res. Clin. Oncol. 119:273–78.*
Rékási et al 1991. Endocrinology 132(5):1991–2000.*
Kaetsu et al, 1987, J. Controlled Red. 6:249–263.*
Vincze et al, 1996, Cancer Detection & Prevention 20(2):153–159.*
Pályi et al. 1996. Cancer Detection & Prevention 20(2):146–152.*
Jung et al, J. Cathol. Med. Cell 43(1):161–170, Abstract Only, 1990.*
Dutta et al, Pharm. Med. 7/1:9–28, 1993.*
Tenover et al. J. Clin. Endocrinol. Metabol. 71/4:881–888, 1990.*
Winkel, Postgraduate Med. 95(6):111–118, May 1994.*
Fraser, H.M. "Effects of Antibodies to Luteinsing Hormone Releasing Hormone on Reproductive Functions in Rodents", in Imm. Horm. Repr. Res., Nieschlag ed., pp. 107–117, 1975.
Stevens et al. "The Identification of Peptide Sequences of Human Chorionic Gonadotropin Containing a Conformational Epitope", Imm. Let. 12: 11–18, 1986.

(List continued on next page.)

Primary Examiner—Nita Minnifield
(74) Attorney, Agent, or Firm—White & Case LLP

(57) ABSTRACT

Immunogenic compositions capable of generating an immune response in mammals against GnRH are disclosed. The immunogenic compositions are effective in methods of treating gonadotropin and gonadal steroid hormone dependent diseases and immunological contraception of mammals.

10 Claims, 9 Drawing Sheets

U.S. PATENT DOCUMENTS

| | | | | |
|---|---|---|---|---|
| 4,879,112 | | 11/1989 | Silversides | 424/85.9 |
| 4,975,420 | | 12/1990 | Silversides | 514/15 |
| 5,023,077 | | 6/1991 | Gevas et al. . | |
| 5,036,047 | | 7/1991 | Mia | 514/15 |
| 5,109,026 | | 4/1992 | Hoskinson | 514/777 |
| 5,204,108 | | 4/1993 | Illum | 424/434 |
| 5,324,512 | | 6/1994 | Ladd et al. | 424/88 |
| 5,378,688 | * | 1/1995 | Nett et al. . | |
| 5,403,586 | | 4/1995 | Russell-Jones | 424/192.1 |
| 5,422,110 | | 6/1995 | Potter et al. | 424/255.1 |
| 5,484,592 | | 1/1996 | Meloen et al. . | |
| 5,488,036 | * | 1/1996 | Nett et al. . | |
| 5,492,893 | | 2/1996 | Nett et al. . | |
| 5,506,207 | * | 4/1996 | Rivier et al. . | |
| 5,508,383 | * | 4/1996 | Sauer et al. . | |
| 5,519,002 | | 5/1996 | Mia . | |
| 5,633,248 | * | 5/1997 | Kato et al. . | |
| 5,648,340 | * | 7/1997 | Barnea . | |
| 5,661,126 | * | 8/1997 | Donahoe et al. . | |
| 5,684,145 | * | 11/1997 | Van Der Zee et al. . | |
| 5,688,506 | * | 11/1997 | Grimes et al. . | |
| 5,708,155 | | 1/1998 | Potter et al. | 536/23.4 |
| 5,723,129 | | 3/1998 | Potter et al. | 424/200.1 |
| 5,759,551 | | 6/1998 | Ladd et al. | 424/198.1 |
| 5,837,268 | | 11/1998 | Potter et al. | 424/255.1 |
| 5,843,446 | | 12/1998 | Ladd et al. | 424/184.1 |

OTHER PUBLICATIONS

Conn, et al. "Gonadotropin–Releasing Hormone and its Analogues", New Eng. J. Med. 2: 93–103, 1991.

McLachlan, et al. "Clinical aspects of LHRH Analogues in Gynaecology: A Review", J. Obs. Gyn. 93: 431–454.

Singh et al. The dominant role of amide group at C–terminus for recognition of antibody. J. Ster. Biochem. 23(5B): 801–2, 1985.

Fraser, H.M. "Physiological Effects of Antibody to Luteinsing Hormone Releasing Hormone", in Phsiological Effects of Immunity Against Reproductive Hormones, Edwards and Johnson, Eds. Cambridge Univ. Press, pp. 137–165, 1976.

Johnson, et al. "The Regulation of Gonadal Function", in Essential Reproduction, 3rd Ed., pp. 101–154, 1988.

Science and Technology, "Clipping the Stork's Wings", The Economist, pp. 73–78, Jan. 9, 1993.

Fraser, H.M. "Active Immunization of Stumptailed Macague Monkeys Against Luteinising Hormone Releasing Hormone, and its Effects on menstrual cycles, Ovarian Steroids and Positive Feedback", J. Rep. Imm. 5: 173–183, 1983.

Jeffcoate, et al. "Anti–RH Sera in the Investigation of Reproduction", in Physiological Effects of Immunity Against Reproductive Hormones, Edwards and Johnson eds. Cambridge Univ. Press, pp. 121–136, 1976.

Talwar, et al. "A British Control Vaccine is on the Horizon for Family Planning", Ann. Med. 25: 207–212, 1993.

Filicori, M. et al. "GnRH Agonists and Antogonists, Current Clinical Status", Drugs, 35: 63–82, 1988.

Burgus, et al. "Primary Structure of the Ovine Hypothalamic Luteinizing Hormone–Releasing Factor (LRF)", Proc. Natl. Acad. Sci. (USA) 69: 278–282, 1972.

Ladd A. "Progress in the Development of Anti–LHRH Vaccine", Am. J. Reprod. Immunol. 29: 189–194, 1993.

Talwar, et al. "Recent Development in immunocontraception", Am. J. Obstet. Gynocol. 157: 1075–1078, 1987.

Thau, R. "Anti–LHRH and Anti–Pitiutary Gonadotropin Vaccines: their Development and Clinical Applications", Scand. J. Immuol. 36: 127–130, 1992.

Marini et al. "A simple method for increasing hapten immuno–genicity by a specific structural modofication of the carrier", J. Immunol. 120: 57–63, 1989.

* cited by examiner

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (ix) FEATURE:
      (A) NAME/KEY: Modified site
      (B) LOCATION: 1
      (C) OTHER INFORMATION: /note= Xaa /note= "pyroglutamic acid"

(ix) FEATURE:
      (A) NAME/KEY: Modified site
      (B) LOCATION: 10
      (C) OTHER INFORMATION: /note= Xaa /note= "amidated glycine"

(ix) FEATURE:
      (A) NAME/KEY: Peptide
      (B) LOCATION: 1..10
      (D) OTHER INFORMATION: /note= "Gonadotropin releasing hormone (GnRH)"

(xi) SEQUENCE DESCRIPTION: SEQ ID NO:1:

Xaa His Trp Ser Tyr Gly Leu Arg Pro Xaa
1               5                           10

(2) INFORMATION FOR SEQ ID NO:2:

(i) SEQUENCE CHARACTERISTICS:
      (A) LENGTH: 16 amino acids
      (B) TYPE: amino acid
      (D) TOPOLOGY: linear (ii) MOLECULE TYPE: peptide (ix) FEATURE:
      (A) NAME/KEY: Modified site

```
            (B) LOCATION: 1
            (C) OTHER INFORMATION: /note= Xaa /note= "pyroglutamic acid"

(ix) FEATURE:
            (A) NAME/KEY: Region
            (B) LOCATION: 1..10
            (D) OTHER INFORMATION: /note= "immunomimic"

(ix) FEATURE:
            (A) NAME/KEY: Region
            (B) LOCATION: 11..16
            (D) OTHER INFORMATION: /note= "spacer"

(xi) SEQUENCE DESCRIPTION: SEQ ID NO:2:

Xaa His Trp Ser Tyr Gly Leu Arg Pro Gly Arg Pro Pro Pro Pro Cys
1               5                   10                  15

(2) INFORMATION FOR SEQ ID NO:3:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (v) FRAGMENT TYPE: N-terminal (ix) FEATURE:
            (A) NAME/KEY: Modified site
            (B) LOCATION: 1
            (C) OTHER INFORMATION: /note= Xaa /note= "pyroglutamic acid"

(ix) FEATURE:
            (A) NAME/KEY: Peptide
            (B) LOCATION: 1..10
            (D) OTHER INFORMATION: /note= "immunomimic"

(xi) SEQUENCE DESCRIPTION: SEQ ID NO:3:

Xaa His Trp Ser Tyr Gly Leu Arg Pro Gly
1               5                   10

(2) INFORMATION FOR SEQ ID NO:4:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: C-terminal (ix) FEATURE:
            (A) NAME/KEY: Peptide
            (B) LOCATION: 1..6
            (D) OTHER INFORMATION: /note= "spacer"

(xi) SEQUENCE DESCRIPTION: SEQ ID NO:4:

Arg Pro Pro Pro Pro Cys
1               5

(2) INFORMATION FOR SEQ ID NO:5:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (ix) FEATURE:
            (A) NAME/KEY: Region
```

```
            (B) LOCATION: 1..7
            (D) OTHER INFORMATION: /note= "spacer"

(ix) FEATURE:
            (A) NAME/KEY: Region
            (B) LOCATION: 8..17
            (D) OTHER INFORMATION: /note= "immunomimic"

(ix) FEATURE:
            (A) NAME/KEY: Modified site
            (B) LOCATION: 17
            (C) OTHER INFORMATION: /note= Xaa /note= "amidated glycine"

(xi) SEQUENCE DESCRIPTION: SEQ ID NO:5:

Cys Pro Pro Pro Pro Ser Ser Glu His Trp Ser Tyr Gly Leu Arg Pro
1               5                   10                  15

Xaa (2) INFORMATION FOR SEQ ID NO:6:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1
            (C) OTHER INFORMATION: /note= Xaa /note= "pyroglutamic acid"

(ix) FEATURE:
            (A) NAME/KEY: Region
            (B) LOCATION: 1..10
            (D) OTHER INFORMATION: /note= "immunomimic"

(ix) FEATURE:
            (A) NAME/KEY: Region
            (B) LOCATION: 11..17
            (D) OTHER INFORMATION: /note= "spacer"

(xi) SEQUENCE DESCRIPTION: SEQ ID NO:6:

Xaa His Trp Ser Tyr Gly Leu Arg Pro Gly Ser Ser Pro Pro Pro Pro
1               5                   10                  15

Cys (2) INFORMATION FOR SEQ ID NO:7:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (ix) FEATURE:
            (A) NAME/KEY: Region
            (B) LOCATION: 1..6
            (D) OTHER INFORMATION: /note= "spacer"

(ix) FEATURE:
            (A) NAME/KEY: Region
            (B) LOCATION: 7..16
            (D) OTHER INFORMATION: /note= "immunomimic"

(ix) FEATURE:
            (A) NAME/KEY: Modified site
            (B) LOCATION: 16
            (C) OTHER INFORMATION: /note= Xaa /note= "amidated glycine"

(xi) SEQUENCE DESCRIPTION: SEQ ID NO:7:
```

```
Cys Pro Pro Pro Pro Arg Glu His Trp Ser Tyr Gly Leu Arg Pro Xaa
1               5                   10                  15
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: C-terminal (ix) FEATURE:
        (A) NAME/KEY: Peptide
        (B) LOCATION: 1..10
        (D) OTHER INFORMATION: /note= "immunomimic"

(ix) FEATURE:
        (A) NAME/KEY: Modified site
        (B) LOCATION: 10
        (C) OTHER INFORMATION: /note= Xaa /note= "amidated glycine"

(xi) SEQUENCE DESCRIPTION: SEQ ID NO:8:

```
Glu His Trp Ser Tyr Gly Leu Arg Pro Xaa
1               5                   10
```

(2) INFORMATION FOR SEQ ID NO:9:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Peptide
        (B) LOCATION: 1..7
        (D) OTHER INFORMATION: /note= "spacer"

(xi) SEQUENCE DESCRIPTION: SEQ ID NO:9:

```
Cys Pro Pro Pro Pro Ser Ser
1               5
```

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: C-terminal (ix) FEATURE:
        (A) NAME/KEY: Peptide
        (B) LOCATION: 1..7
        (D) OTHER INFORMATION: /note= "spacer"

(xi) SEQUENCE DESCRIPTION: SEQ ID NO:10:

```
Ser Ser Pro Pro Pro Pro Cys
1               5
```

(2) INFORMATION FOR SEQ ID NO:11:

(i) SEQUENCE CHARACTERISTICS:
        (A) LENGTH: 6 amino acids

```
            (B) TYPE: amino acid
            (D) TOPOLOGY: linear (ii) MOLECULE TYPE: peptide (v) FRAGMENT TYPE: N-terminal (ix) FEATURE:
            (A) NAME/KEY: Peptide
            (B) LOCATION: 1..6
            (D) OTHER INFORMATION: /note= "spacer"

(xi) SEQUENCE DESCRIPTION: SEQ ID NO:11:

Cys Pro Pro Pro Pro Arg
1               5
```

METHODS FOR THE TREATMENT OF HORMONE-DEPENDENT TUMORS WITH IMMUNOGENS AGAINST GONADOTROPIN RELEASING HORMONE

This is a continuation-in-part of application Ser. No. 08/188,223 filed Jan. 27, 1994 now U.S. Pat. No. 5,688,506.

BACKGROUND OF THE INVENTION

Gonadotropin Releasing Hormone ("GnRH", also known as Luteinizing Hormone Releasing Hormone, or "LHRH"), is of central importance to the regulation of fertility. Johnson M., Everitt B. *Essential Reproduction,* 3rd Edn. Blackwell Scientific Publications, 1988. In males and females, GnRH is released from the hypothalamus into the bloodstream and travels via the blood to the pituitary, where it induces the release of the gonadotropins, luteinizing hormone and follicle stimulating hormone, by gonadotrophs. These two gonadotropins, in turn, act upon the gonads, inducing steroidogenesis and gametogenesis. Steroids released from the gonads into the circulation subsequently act upon various tissues.

The gonadotropin hormonal cascade can be halted by neutralization of the biological activity of GnRH. Fraser H. M. Physiological Effects of Antibody to Leutenizing Hormone Releasing Hormone. In: *Physiological Effects of Immunity Against Reproductive Hormones,* Edwards and Johnson, Eds. Cambridge University Press, 1976. As a consequence of GnRH neutralization, the gonadotropins and gonadal steroids are not released into the blood and their biological activities are thereby eliminated. By eliminating the biological activity of GnRH, the hormonal regulation of fertility is interrupted and gametogenesis ceases. GnRH neutralization halts the production of gametes. GnRH neutralization is thus an effective means of contraception.

A number of important diseases are affected by gonadotropins and gonadal steroid hormones, particularly the gonadal steroids. Such diseases include breast cancer, uterine and other gynecological cancers, endometriosis, uterine fibroids, prostate cancer and benign prostatic hypertrophy, among others. Removal of the gonadal steroid hormonal stimuli for these diseases constitutes an important means of therapy. An effective method of accomplishing this is by neutralizing GnRH, the consequence of which is the elimination of gonadal steroids that induce and stimulate these diseases. McLachlan R. I., Healy D. L., Burger G. B. 1986. Clinical Aspects of LHRH Analogues in Gynaecology: a Review, *British Journal of Obstetrics and Gynaecology,* 93:431–454. Conn P. M., Crowley W. F. 1991. Gonadotropin-Releasing Hormone and Its Analogs, *New England Journal of Medicine.* 324:93–103. Filicori M., Flamigni C. 1988. GnRH Agonists and Antagonists, Current Clinical Status. *Drugs.* 35:63–82.

One effective means of neutralizing GnRH is the induction or introduction of anti-GnRH antibodies in the host or patient. Such antibodies can be induced by active immunization with GnRH immunogens or by passive immunization by administering anti-GnRH antibodies. Fraser H. M. Physiological Effects of Antibody to Leutenizing Hormone Releasing Hormone. In: *Physiological Effects of Immunity Against Reproductive Hormones,* Edwards and Johnson, Eds. Cambridge University Press, 1976. Since anti-GnRH antibodies can neutralize the biological activity of GnRH, immunization constitutes an important approach towards treating diseases dependent upon gonadal steroids and other reproductive hormones as well as a means to regulate mammalian fertility.

GnRH has the same amino acid sequence in all mammals (pGlu-His-Trp-Ser-Tyr-Gly-Leu-Arg-Pro-GlyNH$_2$) (SEQ ID NO: 1 in the Sequence Listing), thus a single immunogen would be effective in all mammalian species, including humans. Active immunization against GnRH, however, has not been practicable due to deficiencies associated with the GnRH immunogens. The prior art anti-GnRH immunogens are not of sufficient potency, and therefore must be administered repeatedly to induce effective levels of anti-GnRH antibodies. In addition, they have not proven to be reliable, in terms of inducing anti-GnRH antibodies in an acceptable portion of the immunized population.

SUMMARY OF THE INVENTION

The present invention concerns methods for the treatment of gonadotropin and gonadal steroid hormone-dependent cancers such as breast, uterine, endometrial, prostatic cancers, and other hormone-dependent disorders such as, endometriosis, uterine fibroids, benign prostatic hypertrophy, etc. The methods comprise the administration to a patient of the inventive immunogens against GnRH which elicit a sufficient titer of anti-GnRH antibodies in the patient to physiologically neutralize so as to limit the cancer-trophic hormone levels in the patient. The physiological neutralization of GnRH inhibits the release of gonadal hormones and therefore, arrests or inhibits tumor growth. Since the methods of the invention inhibit the release of estrogen, thereby inhibiting the growth of the estrogen-dependent tumor cells, it is particularly suited for the treatment of estrogen related breast cancers.

The improved immunogens against GnRH of the present invention induce neutralizing titers of anti-GnRH antibodies in response to a single administration of the immunogen in all of the immunized populations that we have studied. The immunogens of the invention may to be used to treat steroid hormone-dependent diseases and may also be used as immunocontraceptives to regulate fertility.

The immunogens comprise peptides composed of two functional regions: the immunomimic region and a spacer region. The function of the immunomimic which immunologically crossreacts with GnRH is to induce antibodies that bind to the targeted hormone. The spacer element of the peptide serves as a link through which the immunomimic is attached to an immunological carrier, such as diphtheria toxoid ("DT") and also affects the immune response generated by the vaccinated mammal against the immunomimic. For example, in a specific embodiment of the invention, the immunogen peptide has the sequence: pGlu-His-Trp-Ser-Tyr-Gly-Leu-Arg-Pro-Gly-Arg-Pro-Pro-Pro-Pro-Cys (SEQ ID NO: 2 in the Sequence Listing). In this ("GnRH(1–10)-Arg10") peptide, the sequence pGlu-His-Trp-Ser-Tyr-Gly-Leu-Arg-Pro-Gly- (SEQ ID NO: 3 in the Sequence Listing), comprises the immunomimic of GnRH. The remainder of the peptide's sequence, -Arg-Pro-Pro-Pro-Pro-Cys (SEQ ID NO: 4 in the Sequence Listing), constitutes the spacer, which is attached to amino acid number 10 of the GnRH immunomimic.

In one embodiment of the invention, the method of treatment of the hormone-dependent breast cancer comprises passive immunization in which antibodies against GnRH are administered to the patient in a sufficient concentration to reduce free circulating GnRH levels. The anti-GnRH antibodies by binding to GnRH inhibit the release of GnRH-induced pituitary gonadotropins, i.e., Luteinizing Hormone (LH) and Follicle-Stimulating Hormone (FSH) from the pituicytes and therefore, inhibit the release of gonadal hormones. In a preferred embodiment of this aspect of the invention, the anti-GnRH antibodies for human therapy are humanized or human antibodies which may be produced by methods well known to those of ordinary skill in the art. The immunogens induce the inhibition of the release of the gonadal hormones such as estrogen thereby inhibiting the growth of hormone-dependent tumor cells. Specifically, in an estrogen-dependent breast tumor, the administration of the antibodies leads to the inhibition of the release of estrogen, thereby arresting or slowing the growth of the estrogen-dependent tumor cell.

In another embodiment, the invention concerns a method for the treatment of hormone-dependent breast cancer by active immunization, comprising administering to a patient an immunogen or a pharmaceutical composition containing an immunogen which comprises peptide immunomimics of GnRH which are associated with spacer sequences and coupled to immunological carriers, such as DT. In this method of immunization against breast cancer, the immunogen is capable of inducing an immune response in which the patient produces antibodies at a titer sufficient to neutralize the physiological function the patient's own GnRH. The neutralization of GnRH by the binding of the anti-GnRH antibodies to GnRH in the patient leads to the inhibition of the release of gonadal hormones, i.e., estrogen, testosterone, etc., in the patient and therefore, the inhibition of the gonadal hormone-dependent tumor growth.

In the methods of the invention comprising active immunization, the immunogens comprise two peptide immunomimics of GnRH that are associated with four spacer sequences. Methods of coupling these peptides to immunological carriers, such as DT, to yield anti-GnRH immunogens are provided. The immunogens may be used singly or in combination to induce anti-GnRH antibody responses in the vaccinated mammal. As compared to the prior art anti-GnRH immunogens, the immunogens of the present invention induce a biologically effective immune response following a single administration of immunogen in all of the immunized animals tested. The immunogens can be administered in different physical forms, including soluble and precipitate. The immunomimic spacer peptides of this invention can be coupled to immunological carriers over a wide range of peptide to carrier substitution ratios and yield effective immunogens.

DETAILED DESCRIPTION OF THE INVENTION

EXAMPLE 1

Figure 1:
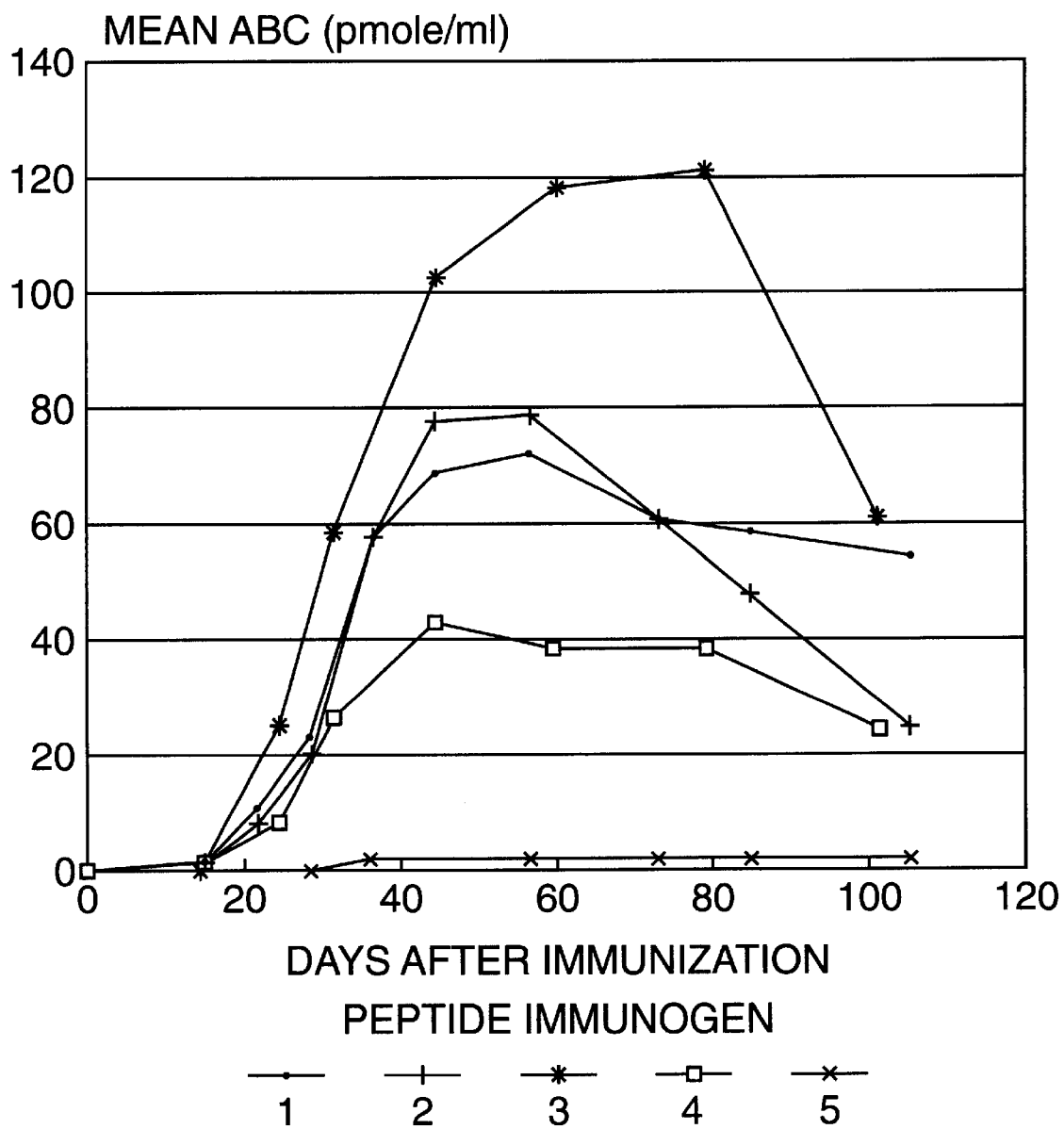
FIG. 1: Depicts anti-GnRH antibody responses to the administration of the inventive immunogens comprising peptides 1–4 and the comparative prior art anti-GnRH immunogen, peptide 5 as measured by mean antigen binding capacities ("ABC") in picomoles per milliliter with respect to days after immunization in immunized rabbits.

Peptides with the amino acid sequences listed in Table 1 were synthesized and prepared by standard solid phase synthesis methods. Each peptide was characterized as to amino acid content and purity.

TABLE 1

| Peptide Designation | | Amino Acid Sequence |
|---|---|---|
| 1 | GnRH (1–10)-Serl | Cys-Pro-Pro-Pro-Pro-Ser-Ser-Glu-His-Trp-Ser-Tyr-Gly-Leu-Arg-Pro-Gly($NH_2$) (SEQ ID NO: 5 in the Sequence Listing) |
| 2 | GnRH(1–10)-Ser 10 | pGlu-His-Trp-Ser-Tyr-Gly-Leu-Arg-Pro-Gly-Ser-Ser-Pro-Pro-Pro-Pro-Cys (SEQ ID NO: 6 in the Sequence Listing) |

TABLE 1-continued

| Peptide | Designation | Amino Acid Sequence |
|---|---|---|
| 3 | GnRH(1–10)-Arg 1 | Cys-Pro-Pro-Pro-Pro-Arg-Glu-His-Trp-Ser-Tyr-Gly-Leu-Arg-Pro-Gly(NH2) (SEQ ID NO: 7 in the Sequence Listing) |
| 4 | GnRH(1–10)-Arg 10 | pGlu-His-Trp-Ser-Tyr-Gly-Leu-Arg-Pro-Gly-Arg-Pro-Pro-Pro-Pro-Cys (SEQ ID NO: 2 in the Sequence Listing) |

Each of peptides 1–4 contains an immunomimic of GnRH that is either preceded by or followed by a spacer. Two immunomimics of GnRH were used: pGlu-His-Trp-Ser-Tyr-Gly-Leu-Arg-Pro-Gly-(SEQ ID NO: 3 in the Sequence Listing), (peptides 2 and 4 Table 1) wherein the spacer was attached through the carboxy terminal end of GnRH (amino acid #10); and, -Glu-His-Trp-Ser-Tyr-Gly-Leu-Arg-Pro-Gly (NH$_2$) (SEQ ID NO: 8 in the Sequence Listing), (peptides 1 and 3 Table 1) wherein the spacer was attached at the amino terminal end of GnRH (amino acid #1).

The four spacers set forth in Table 2 were used.

TABLE 2

| Spacer Designation | Amino Acid Sequence |
|---|---|
| Ser 1 | Cys-Pro-Pro-Pro-Pro-Ser-Ser- (SEQ ID NO: 9 in the Sequence Listing) |
| Ser 10 | -Ser-Ser-Pro-Pro-Pro-Pro-Cys (SEQ ID NO: 10 in the Sequence Listing) |
| Arg 1 | Cys-Pro-Pro-Pro-Pro-Arg- (SEQ ID NO: 11 in the Sequence Listing) |
| Arg 10 | -Arg-Pro-Pro-Pro-Pro-Cys (SEQ ID NO: 4 in the Sequence Listing) |

The numerals 1 and 10 in the spacer designation refer to the GnRH amino acid number to which the spacer is attached. While these spacer regions of the molecules have been set forth separately in Table 2, in the preferred embodiment of the invention the peptide is synthesized as one continuous peptide sequence molecule.

Each of these peptides 1–4 of Table 1 was conjugated to amino groups present on a carrier such as Diphtheria Toxoid ("DT") via the terminal peptide cysteine residue utilizing heterobifunctional linking agents containing a succinimidyl ester at one end and maleimide at the other end of the linking agent.

To accomplish the linkage between any of the Peptides 1–4 above and the carrier, the cysteine of the peptide was first reduced. The dry peptide was dissolved in 0.1 M sodium phosphate buffer (degassed), pH 8.0, with a thirty molar excess of dithiothreitol ("DTT"). The solution was stirred under a water saturated nitrogen gas atmosphere for three hours at room temperature. An additional 15 molar excess DTT was added and the mixture was stirred an additional hour at room temperature under water saturated nitrogen gas. The peptide containing reduced cysteine was separated from the other components by chromatography at 4° C. over a G10 Sephadex column equilibrated with 0.2 M acetic acid. The peptide was lyophilized and stored under vacuum until used.

The DT was activated for coupling to the peptide by treatment with the heterobifunctional linking agent epsilon-maleimidocaproic acid N-hydroxysuccinimide ester ("EMCS"), in proportions sufficient to achieve activation of approximately 25 free amino groups per $10^5$ molecular weight of DT. In the specific instance of DT, this amounted to the addition of 6.18 mg of EMCS (purity 98%) to each 20 mg of DT.

Activation of DT was accomplished by dissolving each 20 mg aliquot of DT in 1 ml of 0.5 M sodium phosphate buffer, pH 6.6. Aliquots of 6.18 mg EMCS were dissolved into 0.2 ml of dimethylformamide. Under darkened conditions, the EMCS was added dropwise in 50 microliter ("$\mu$l") amounts to the DT with stirring. After 90 minutes incubation at room temperature in darkness, the mixture was chromatographed at 4° C. on a G50 Sephadex column equilibrated with 0.1 M sodium citrate buffer, pH 6.0, containing 0.1 mM ethylenediaminetetraacetic acid disodium salt ("EDTA"). (Column=1.5×120 cm; flow rate=8 ml/hr; fraction size=2 ml). The fractions' $A_{260}$ were determined using a spectrophotometer, enabling the fractions containing DT to be identified.

Fractions containing the EMCS activated DT were pressure concentrated over a PM 10 ultrafiltration membrane under nitrogen gas in conditions of darkness. The protein content of the concentrate was determined by the BCA method (PIERCE, Ill., USA). The EMCS content of the carrier was determined by incubation of the activated DT with cysteine-HCl followed by reaction with 100 $\mu$l of 10 mM Elman's Reagent (5, 5, dithio-bis (2-nitrobenzoic acid)). The optical density difference between a blank tube containing cysteine-HCl and the sample tube containing cysteine-HCl and carrier was translated into EMCS group content by using the molecular extinction coefficient of $13.6\times10^3$ for 5-thio-2-nitro-benzoic acid at 412 nm.

The reduced cysteine content ("-SH") of the peptide was also determined utilizing Elman's Reagent. Approximately 1 mg of peptide was dissolved in 1 ml of nitrogen gas saturated water and a 0.1 ml aliquot of this solution was reacted with Elman's Reagent. Utilizing the molar extinction coefficient of 5-thio-2-nitro-benzoic acid ($13.6\times10^3$), the free cysteine -SH was calculated.

The reduced peptide was then coupled to the activated DT. An amount of peptide containing sufficient free -SH to react with a selected proportion of the EMCS activated amino groups on the DT was dissolved in 0.1 M sodium citrate buffer, pH 6.0, containing 0.1 mM EDTA, and added dropwise to the EMCS activated DT under darkened conditions. After all the peptide solution had been added to the activated DT, the mixture was incubated overnight in the dark under a water saturated nitrogen gas atmosphere at room temperature.

The conjugate of the peptide linked to DT via EMCS was separated from other components of the mixture by low pressure chromatography at 4° C. over a G50 Sephadex column equilibrated with 0.2 M ammonium bicarbonate (column=1.5×120 cm, flow rate=1.8 ml/15 min., fraction size=1.8 ml). The conjugate eluted in the column void volume (detected by $A_{280}$ measurements) and was lyophilized and stored desiccated at −20° C. until used.

The conjugate may be characterized as to peptide content by a number of methods known to those skilled in the art including weight gain, amino acid analysis, etc. Various substitution ratios of peptide to DT were accurately and reproducibly obtained by (1) varying the quantity of EMCS added to activate the DT, and/or, (2) varying the quantity of reduced peptide added to the EMCS activated DT. For example, the activation of DT with a ratio of 31 moles EMCS to 1 mole of 100,000 molecular weight DT adds 12±2 EMCS groups per 100,000 molecular weight of DT. The addition of 14 peptide groups per 100,000 molecular weight of this activated DT resulted in a substitution ratio of 12±2 peptides per 100,000 molecular weight of DT. Conjugates of Peptides 1–4 to DT produced by these methods were determined by amino acid analysis to have 4–30 moles of peptide per $10^5$ MW of DT. All of the conjugates were considered suitable as immunogens for immunization of test animals.

EXAMPLE 2

For comparative purposes a prior art GnRH immunogen ("peptide 5") was constructed wherein the peptide immunomimic of GnRH did not contain a spacer element. Peptide 5 had the sequence: Glu-His-Trp-Ser-Tyr-Gly-Leu-Arg-Pro-GlyNH$_2$ (SEQ ID NO: 8 in the Sequence Listing).

The peptide was activated with m-Maleimidobenzoyl N-Hydroxysuccinimide Ester ("MBS"). 20.0 mg of [glu 1]-GnRH were dissolved in 1.0 ml of N,N-Dimethylformamide ("DMF"). To this solution was added 5.31 mg MBS dissolved in 1.0 ml DMF. The combined solution was stirred overnight at room temperature in the dark.

40.0 mg of DT was dissolved in 10.0 ml of Sodium Carbonate Buffer (0.2 M, pH=9.0), containing 2.2 mg of 2-Iminothiolane HCl ("2-IT"). The solution containing the MBS-activated GnRH was then slowly added to the DT/2-IT solution, and the mixture was stirred slowly for 8 hours at room temperature in the dark.

The conjugate was purified by column chromatography over Sephadex G50 (column: 1.5×100 cm; buffer: Ammonium Bicarbonate, 0.2 M; fractions: 2.6 ml, every 15 minutes) with identification of the fractions containing conjugate by spectrophotometry ($A_{254}$). G50 purified conjugate was lyophilized and stored desiccated at −20° C. until used. The peptide DT substitution ratio of the Immunogen 5 conjugate was determined by amino acid analysis to be 13 peptides per $10^5$ molecular weight of DT.

EXAMPLE 3

Different groups of female rabbits were each immunized with one of the conjugates, peptides 1–5 of Examples 1 and 2. Each conjugate was dissolved to a concentration of 2.0 mg/ml in phosphate buffered saline (0.2 M, pH=7.2) containing 200 μg/ml of norMDP adjuvant. The conjugates comprising peptides 1,2,3 and 4 of Example 1 did not completely dissolve in the buffer; the conjugate of peptide 5 of Example 2 did completely dissolve in the buffer. Each mixture was emulsified with an equal volume of Squalene-Arlacel (4:1 ratio, volume of Squalene: volume of Arlacel) to prepare an immunogen formulation which contained 1.0 mg/ml conjugate and 100 μg/ml norMDP. 1.0 ml of immunogen was injected into each rabbit, administered into the rear leg muscles (2 sites, 0.5 ml/site), on day 0 of the test. Blood was collected from each rabbit prior to immunization on day 0, and on selected days thereafter. Serum was prepared from each blood sample and stored frozen at −20° c. until utilized in assays to determine the presence of anti-GnRH antibodies.

A liquid phase Radioimmunoassay (RIA) was used to detect and quantify anti-GnRH antibodies. In the RIA, 0.04, 0.2, 1.0 or 5.0 μl aliquots of antiserum were incubated with approximately 150 fmole of 3H labeled GnRH (specific activity=53.2 Ci/mmole) in a total volume of 400 μl. Dilutions were made in FTA Hemagglutination Buffer (BBL, Becton Dickinson Microbiology Systems, MD, USA) containing 1% bovine serum albumin. The antisera were incubated with labeled hormone for 2 hours at room temperature. A 0.1 ml aliquot of heat inactivated (56° C., 30 min) fetal calf serum (cooled to 2–8° C.) was then added to each tube, following which the antibody-hormone complexes were precipitated by the addition of 0.5 ml of 25% polyethylene glycol (MW=8,000 gm/mole) (cooled to 2–8° C.). The precipitates were pelleted by centrifugation (30 minutes at 1500×g), the supernatants were discarded, and the pellets were counted by liquid scintillation counting to measure the quantity of radioactivity contained therein. Antigen binding capacities (ABC) for each antiserum were then determined from the amount of radioactive hormone precipitate after substraction of nonspecific background binding (determined by preincubation of the antisera dilution with excess amounts (~$10^5$ fold) of the hormone). Inhibition of the antisera with the excess quantity of unlabeled hormone also established the specificity of the antisera for GnRH. Serum taken from the rabbits prior to immunization served as nonimmunized (normal) controls.

The mean ABCs measured in the sera from rabbits immunized with the conjugated peptides of Examples 1 and 2 are shown in Table 3 and in FIG. 1. As the results show, a single administration of the immunogens comprising peptides 1,2,3 and 4 of Example 1 induced rapid and potent antibody responses against GnRH.

TABLE 3

RABBIT ANTI-GNRH ANTIBODY RESPONSES INDUCED BY ONE ADMINISTRATION OF PEPTIDE CONJUGATE

| Peptide | Peptide:DT Substitution Ratio | Rabbit Sera ABC (mean) [pmoles/ml] | | | | | | | | |
|---|---|---|---|---|---|---|---|---|---|---|
| | | Day 0 | Day 14 | Day 21 | Day 28 | Day 36 | Day 44 | Day 56 | Day 73 | Day 85 | Day 105 |
| 1 | 13 | 0 | 0.30 | 10.83 | 22.63 | 57.23 | 68.93 | 72.13 | 61.23 | 58.73 | 54.03 |
| 2 | 13 | 0 | 0.27 | 7.52 | 19.83 | 57.63 | 77.83 | 78.73 | 60.83 | 47.90 | 24.93 |

TABLE 3-continued

RABBIT ANTI-GNRH ANTIBODY RESPONSES INDUCED
BY ONE ADMINISTRATION OF PEPTIDE CONJUGATE

| 5 | 13 | 0 | 0 |  | 0 | 1.78 |  | 1.60 | 1.51 | 2.00 | 2.10 |
|---|----|---|---|---|---|------|---|------|------|------|------|

|   |    | Day 0 | Day 15 | Day 24 | Day 31 | Day 44 | Day 59 | Day 79 | Day 101 |
|---|----|-------|--------|--------|--------|--------|--------|--------|---------|
| 3 | 11 | 0 | 1.53 | 24.59 | 58.31 | 102.71 | 118.16 | 120.99 | 61.00 |
| 4 | 13 | 0 | 1.77 | 8.90 | 26.03 | 42.88 | 38.25 | 38.30 | 24.35 | n=5 rabbits for Peptides 1,2,3 and 4. n=6 rabbits for peptide 5.

By comparison, the anti-GnRH response induced by a single administration of the peptide 5 immunogen of Example 2 induced a minimal response. This is not because the conjugate constructed with peptide 5 is a poor immunogen; when administered in additional booster immunizations several weeks after the first immunization, the peptide 5 conjugate induces effective levels of anti-GnRH antibodies (of approximately 12–18 pmole/ml ABC). In this regard, the peptide 5 conjugate behaves similarly to standard GnRH immunogens. However, the conjugate constructed with peptide 5 requires more than one administration, induces lower levels of anti-GnRH antibodies, and takes a longer time to elicit effective antibody levels than do the conjugates of peptides 1–4 of Example 1.

These results also demonstrate the critical contribution of the spacer to the immunogenicity of peptides 1,2,3 and 4 of Example 1. Peptide 5 bears the same immunomimic of GnRH as peptides 1 and 3, yet peptide 5 is inferior as an immunogen. This is because peptide 5 does not contain a spacer sequence, which is present in peptides 1 and 3. Thus, the presence of the spacers in peptides 1,2,3 and 4 of Example 1 makes a critical contribution to their enhanced immunogenicity.

EXAMPLE 4

Figure 2:
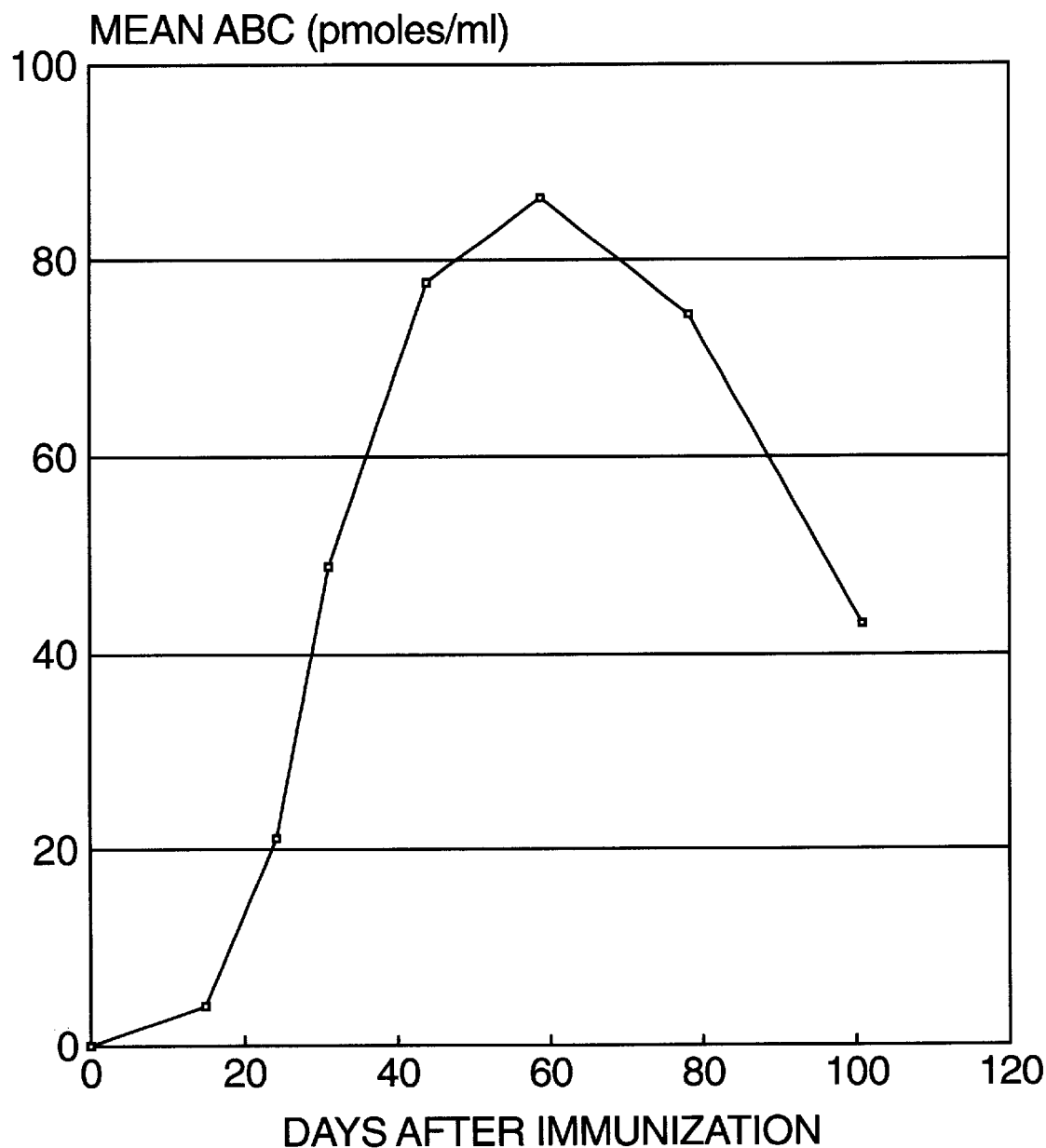
FIG. 2: Depicts the antibody response to immunization with an immunogen comprising a mixture of peptides 3 and 4 as measured by mean ABC with respect to days after immunization.

Conjugates comprising peptides 3 and 4 of Example 1 were mixed 1:1 to give a protein concentration of 2.0 mg/ml in PBS. The mix was then prepared as immunogen and injected into rabbits, as in Example 3. The sera were tested for anti-GnRH antibody by the RIA of Example 3. The results are shown in Table 4 and FIG. 2.

against the carboxy terminal end of GnRH, while the GnRH (1–10)-Arg10 peptide induced antibodies directed against the amino terminal end of GnRH. Thus, conjugates comprising these peptides can be mixed to yield immunogens that induce antibodies against both ends of the target molecule.

EXAMPLE 5

When the peptides of Example 1 are conjugated to DT and prepared as described in Example 1, a proportion of the product is present as a precipitate. The formation of the precipitate is dependent upon various physical parameters, including concentration of conjugate, pH and salt concentration. We prepared a conjugate of peptide 2 of Example 1 to DT as described in Example 1. From this we prepared three fractions of conjugate, based upon solubility. The conjugate was stirred in 0.01 M phosphate buffer pH=7.2 and the insoluble material was collected by centrifugation as Fraction #1. To the soluble material we added NaCl (to 0.5 M) and adjusted the pH to 6.0 with 0.1 M HCl, which yielded additional precipitate that we collected as Fraction #2. The remaining soluble material served as Fraction #3. Each fraction was lyophilized. The percent recoveries (from the 15 mg of starting material) were: Fraction-1, 36%; Fraction-2, 15%; Fraction-3, 27%; lost, 22%. The peptide DT substitution ratios were determined by amino acid analysis and shown to be 14.0 for Fraction 1; 13.7 for Fraction 2; 10.0 for Fraction 3.

Each of the fractions 1–3 were injected into a group of mice, at 6 mice/group. (100 μg conjugate/mouse, with 25 μg

TABLE 4

RABBIT ANTI-GNRH RESPONSES INDUCED BY
ONE ADMINISTRATION OF A MIXTURE OF PEPTIDE CONJUGATES

| | ABC (mean ± s.e.) [pmoles/ml] | | | | | | | |
|---|---|---|---|---|---|---|---|---|
| Day of Test | 0 | 15 | 24 | 31 | 44 | 59 | 79 | 101 |
| ABC | 0 | 4.6 ± 0.7 | 21.6 ± 3.3 | 49.0 ± 9.9 | 77.8 ± 13.0 | 86.0 ± 21.0 | 74.3 ± 22.0 | 43.0 ± 12.0 |

Figure 3:
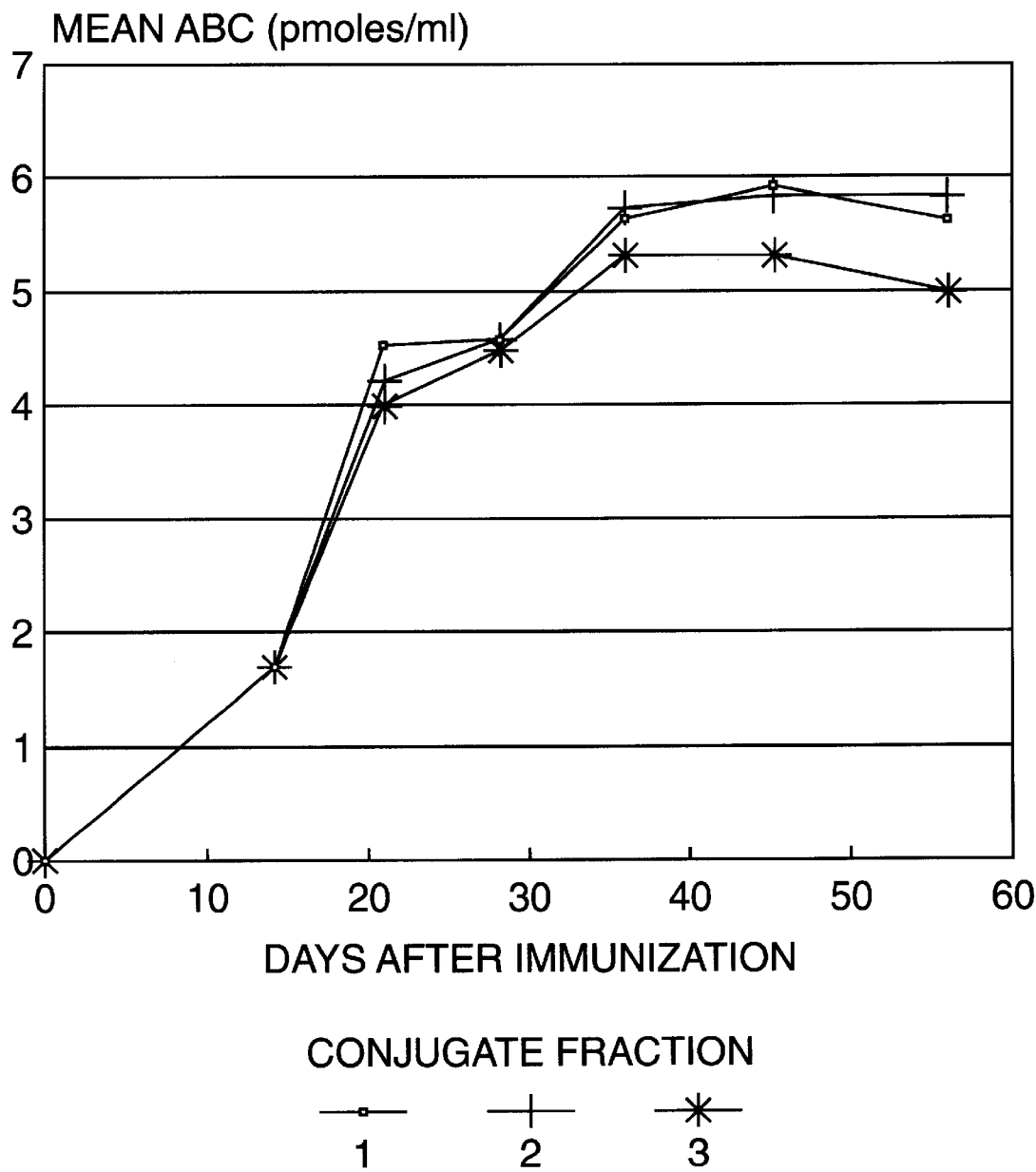
FIG. 3: Depicts the results of immunizations in mice as measured by a mean ABC with respect to days after immunization after immunization with fractions of a preparation of peptide 2 immunogens fractionated on the basis of solubility.

As can be seen from Table 4, effective levels of antibody were induced by the combined administration of the peptide 3 and 4 conjugates. Both peptide components contributed almost equally to the induction of the anti-GnRH antibodies, as shown by antibody specificity testing. The GnRH (1–10)-Arg1 peptide induced antibodies directed predominantly nMDP, in 0.1 ml of a 1:1 mixture of FTA buffer (containing conjugate+adjuvant) to squalene-arlacel, i.p.). The mice received a single injection of immunogen, after which sera samples were obtained at intervals and tested for anti-GnRH antibody by the RIA of Example 3. The results of this test are shown in Table 5 and in FIG. 3.

TABLE 5

ANTI-GnRH RESPONSES OF MICE TO
SOLUBILITY FRACTIONS OF CONJUGATE

| Conjugate Fraction | ABC (mean ± s.e.) [pmoles/ml] | | | | | | |
|---|---|---|---|---|---|---|---|
| | Day 0 | Day 14 | Day 21 | Day 28 | Day 36 | Day 45 | Day 56 |
| 1 | 0 | 1.7 ± 0.3 | 4.5 ± 0.4 | 4.6 ± 0.4 | 5.6 ± 0.4 | 5.9 ± 0.5 | 5.6 ± 0.4 |
| 2 | 0 | 1.7 ± 0.4 | 4.2 ± 0.3 | 4.6 ± 0.2 | 5.7 ± 0.2 | 5.8 ± 0.2 | 5.8 ± 0.2 |
| 3 | 0 | 1.7 ± 0.3 | 4.0 ± 0.3 | 4.5 ± 0.3 | 5.3 ± 0.3 | 5.3 ± 0.3 | 5.0 ± 0.3 |

As the results show, each mouse group produced equally potent anti-GnRH antibody responses. This demonstrates that despite variances in the solubility of conjugates produced from the peptide of Example 1, the soluble and insoluble forms can be administered as immunogens and are of equivalent immunogenicity.

EXAMPLE 6

We constructed conjugates of peptides 1 and 2 of Example 1 to DT as described in Example 1. By varying the quantities of reduced peptide added to DT, we constructed conjugates with different peptide:DT substitution ratios. The substitution ratios, determined by amino acid analysis of the conjugates are shown in Table 6:

TABLE 6

| Conjugate Number | Peptide Used (from Example 1) | Peptide:DT Substitution Ratio |
|---|---|---|
| 6.1 | 1 | 4.7 |
| 6.2 | 1 | 13.1 |
| 6.3 | 1 | 25.9 |
| 6.4 | 2 | 5.1 |
| 6.5 | 2 | 12.8 |
| 6.6 | 2 | 30.1 |

Figure 4:
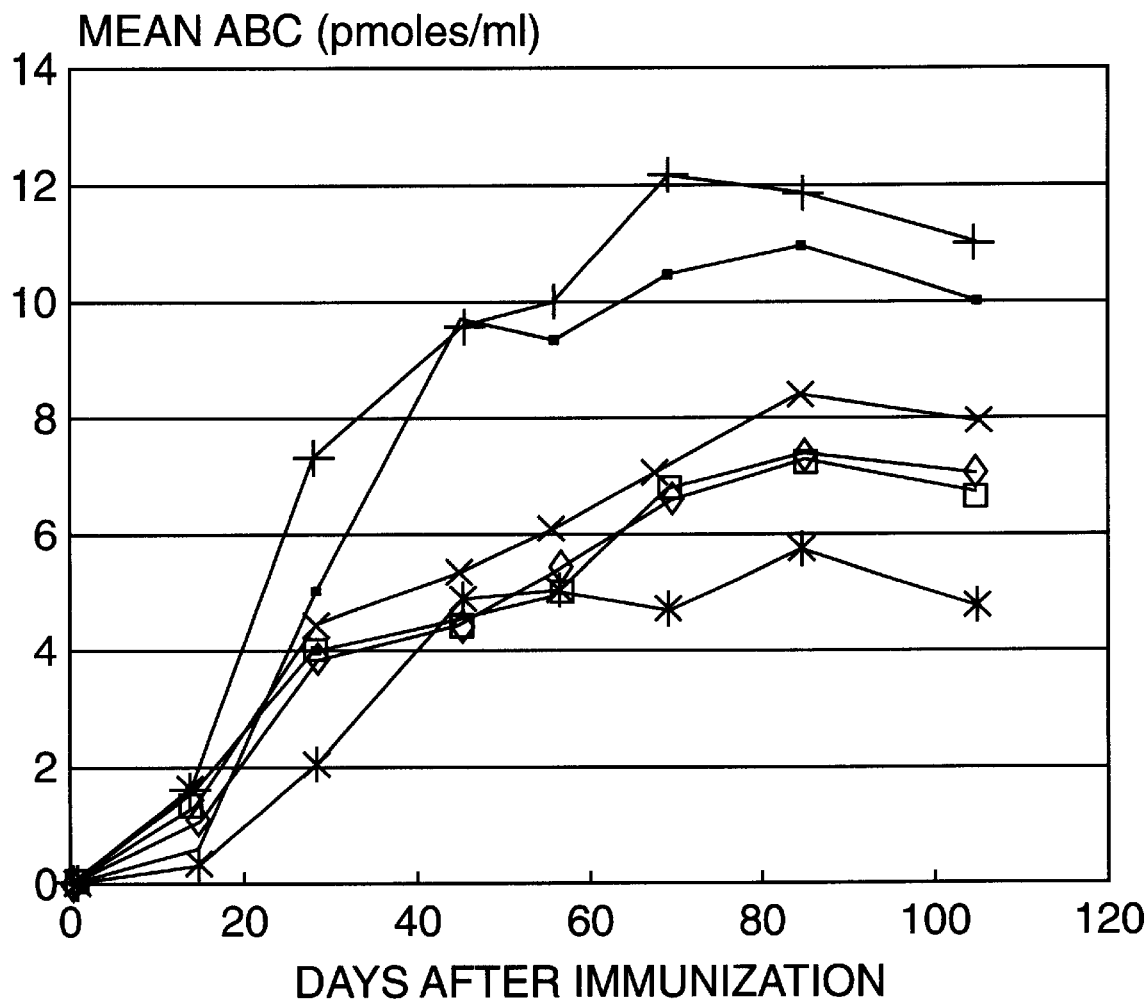
FIG. 4: Depicts antibody responses in mice as measured by mean ABC with respect to days after immunization when immunized with various conjugates of peptides 1 and 2 at different peptide: DT substitution ratios.

Mice were immunized with each conjugate preparation. The immunization and subsequent assay procedures were identical to those described in Example 5 (6 mice/group). The results of this test are shown in Table 7 and in FIG. 4.

EXAMPLE 7

We constructed conjugates of peptides 1 and 2 of Example 1 to DT as described in Example 1. The peptide:DT substitution ratio for peptide 1 (GnRH(1–10)-Ser1) was 13.1:1 and the ratio for peptide 2 (GnRH(1–10)-Ser10) was 12.8:1.

We prepared immunogen by emulsifying aqueous phase (containing a mixture of the two conjugates plus norMDP in PBS) with oily vehicle as described in Example 3. The oily vehicle used was Montanide ISA 703 containing 1.8% aluminum monostearate. "Montanide ISA 703 AMS" is manufactured and sold by SEPPIC, Inc. (Paris, France). The final concentrations of the active components in the immunogen were: GnRH (1–10)-Ser1-DT=0.5 mg/ml; GnRH (1–10)-Ser10-DT=0.5 mg/ml; norMDP=0.1 mg/ml. 1.0 ml of immunogen was injected into each of 3 male rabbits, administered to the rear leg muscles (2 sites/rabbit, 0.5 ml/site), on day 0 of the test. Blood was collected from each rabbit prior to immunization and on selected days thereafter. Serum was prepared from each blood sample and stored frozen at −20° C. until utilized in assays to determine the presence of anti-GnRH antibodies (as described in Example 3).

Figure 5:
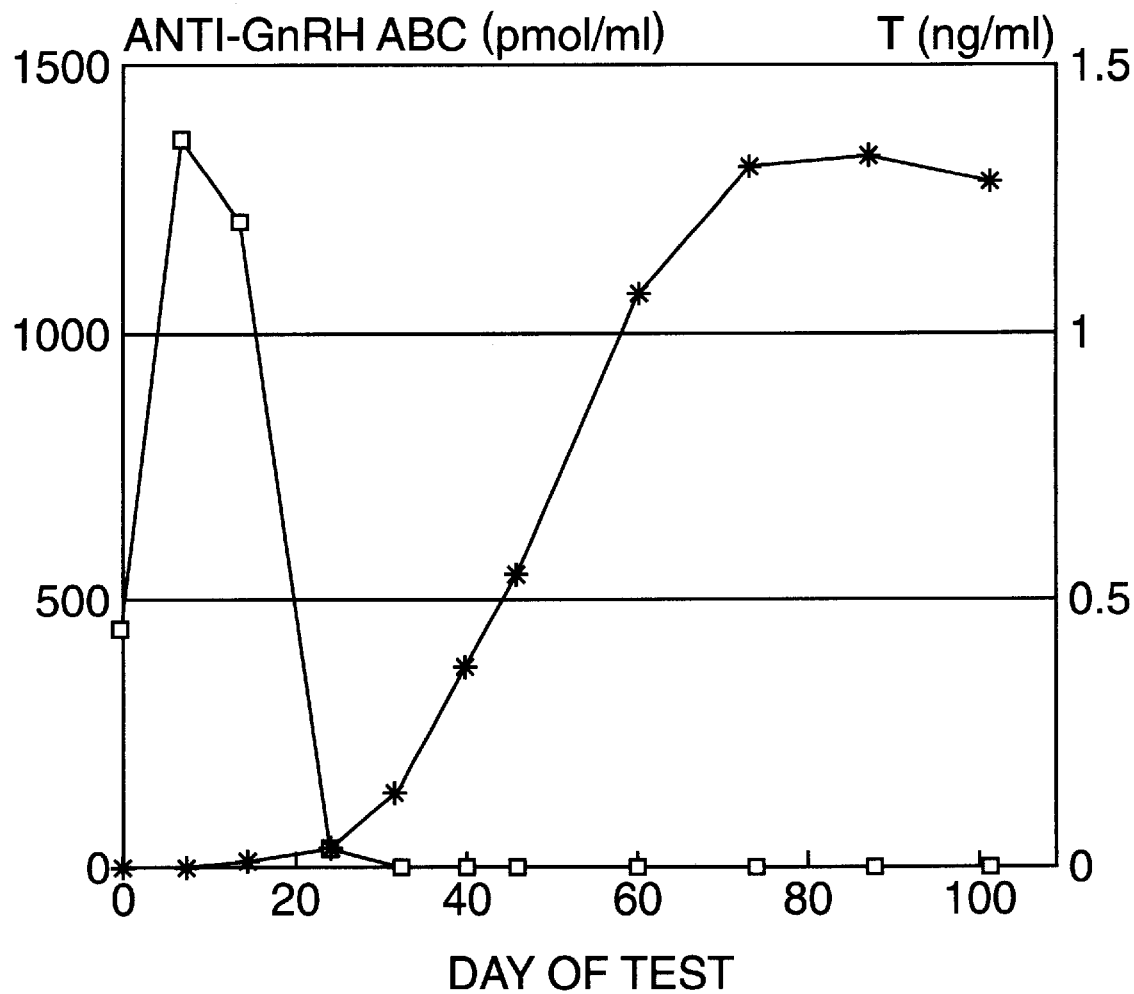
FIG. 5: Depicts antibody responses of male rabbits as measured by mean ABC with respect to days after immunization when immunized with a mixture of conjugates of peptides 1 and 2. Serum testosterone levels in these male rabbits over the course of the immunization test period are shown.

The mean ABC's measured in the sera from these three male rabbits are shown in Table 8 and in FIG. 5. As the results show, a single immunization with the DT conjugates of peptides 1 and 2 of Example 1 in the Montanide ISA 703 containing 1.8% AMS rapidly induced potent antibody responses against GnRH. These anti-GnRH responses are

TABLE 7

ANTI-GnRH RESPONSES OF MICE TO PEPTIDE-CARRIER
CONJUGATES WITH DIFFERENT SUBSTITUTION RATIOS

| Conjugate number | Peptide:DT Substitution Ratio | ABC (mean ± s.e.) [pmoles/ml] | | | | | | | |
|---|---|---|---|---|---|---|---|---|---|
| | | Day 0 | Day 14 | Day 28 | Day 45 | Day 56 | Day 70 | Day 85 | Day 105 |
| 6.1 | 4.7 | 0 | 0.7 ± 0.1 | 5.1 ± 0.4 | 9.8 ± 0.5 | 9.4 ± 0.4 | 10.5 ± 0.6 | 11.0 ± 0.8 | 10.0 ± 1.0 |
| 6.1 | 13.1 | 0 | 1.8 ± 0.3 | 7.4 ± 0.6 | 9.7 ± 0.4 | 10.1 ± 0.2 | 12.2 ± 0.2 | 11.9 ± 0.2 | 11.0 ± 0.2 |
| 6.3 | 25.9 | 0 | 0.4 ± 0 | 2.1 ± 0.5 | 4.9 ± 1.0 | 5.1 ± 1.1 | 4.7 ± 1.3 | 5.7 ± 1.7 | 4.7 ± 1.6 |
| 6.4 | 5.1 | 0 | 1.7 ± 0.6 | 4.1 ± 0.6 | 4.6 ± 0.7 | 5.0 ± 0.6 | 6.8 ± 0.9 | 7.3 ± 1.2 | 6.7 ± 1.1 |
| 6.5 | 12.8 | 0 | 1.4 ± 0.1 | 4.5 ± 0.2 | 5.4 ± 0.3 | 6.1 ± 0.4 | 7.2 ± 0.2 | 8.4 ± 0.3 | 7.9 ± 0.3 |
| 6.6 | 30.1 | 0 | 1.1 ± 0.4 | 3.9 ± 0.4 | 4.6 ± 0.4 | 5.4 ± 0.4 | 6.6 ± 0.5 | 7.4 ± 0.5 | 7.0 ± 0.5 |

As the results show, significant anti-GnRH responses were induced by each of the conjugate preparations. This demonstrates that the peptides of Example 1 can be conjugated to carriers over a broad range of peptide:carrier substitution ratios and yield effective immunogens.

representative of responses induced by the peptide conjugates (individually or mixtures thereof) of this invention when administered with norMDP in an emulsion comprising equal parts aqueous phase and Montanide ISA 703 containing 1.8% AMS.

TABLE 8

| Day | Mean ABC (pmol/ml) (± s.e.) |
|---|---|
| 0 | 0.02 (±0.1) |
| 7 | 0.18 (±0) |
| 14 | 3.71 (±0.8) |
| 24 | 40.3 (±7.7) |
| 32 | 131.5 (±29.1) |
| 40 | 374.7 (±13.1) |
| 46 | 543 (±85.0) |
| 60 | 1061 (±368.2) |
| 74 | 1303.3 (±527.6) |
| 88 | 1320.7 (±602.9) |
| 102 | 1272 (±558.1) |
| — | — |

EXAMPLE 8

The production of gonadal steroids can be assessed as a measure of GnRH-immunogen efficacy in immunized animals. We measured testosterone levels in the serum samples obtained from the three male rabbits of Example 7. The testosterone levels were determined using a radioimmunoassay kit for testosterone determination ("Coat-a-Count", purchased from Diagnostic Products Corp., Los Angeles, Calif., USA). The results presented in Table 9 and in FIG. 5 show the immunogen induced levels of anti-GnRH antibodies that totally inhibited the production of testosterone in the male rabbits.

Testosterone was undetectable in the sera of 2 animals by day 24 of the test, and in all 3 rabbits by day 32. The drop in testosterone serum coincides with the rise in anti-GnRH Ab titer, as can be seen in FIG. 5.

TABLE 9

Testosterone Levels In Immunized Rabbits

| Day | Mean T (ng/ml) (± s.e.) |
|---|---|
| 0 | 0.32 (±0.2) |
| 7 | 1.37 (±0.1) |
| 14 | 1.21 (±0.5) |
| 24 | 0.1 (±0) |
| 32 | 0 |
| 40 | 0 |
| 46 | 0 |
| 60 | 0 |
| 74 | 0 |
| 88 | 0 |
| 102 | 0 |
| — | — |

EXAMPLE 9

In the following examples the effects of the inventive anti-GnRH immunogen were studied on the growth of estrogen-dependent breast tumors as tested with a subline of the MCF-7 human breast cancer cell line generated (Mcf7B (BIM)) tumors in nude mice. The method of passive immunization was used in the experiments on immunoincompetent nude mice, using anti-GnRH antibodies produced in rabbits immunized with the inventive GnRH-Ser conjugate as immunogens. The method comprises the administration of anti-GnRH antibodies to mice bearing detectable tumors. Various positive controls were used in the following experiments including, the widely used and accepted therapy for breast cancer using the anti-estrogen Tamoxifen; a GnRH analog superagonist peptide, decapeptide, also known as decapeptyl which inhibits the release of LH and FSH from the gonadotrophs. The effects of placebo, phosphate-buffered saline solution (PBS), estradiol (E2) and anti-DT antibodies in the human breast tumor xenografts were also tested.

In the experiments, breast tumors were grown in donor nude mice from Mcf7 (B1M) breast cancer cell line. After 7–8 weeks, the tumors were grafted to 62 female nude mice. Following 3 to 4 weeks, the tumor xenografts were evaluated to determine if the size of the tumor was large enough to initiate the therapy. At the start of the experiments, some mice had adverse reactions to anti-DT and anti=GnRH antiserum preparations. Therefore, the therapies with purified anti-DT and purified anti-GnRH antibodies were delayed for several days after Tamoxifen, placebo, E2 and PBS had started, while affinity purified anti-DT and anti-GnRH were prepared. On day 30 of these experiments, two mice were bled by heart puncture for serum antibody studies and tumors were harvested, measured and frozen for receptor studies, etc. The remaining mice were randomly separated into six groups of ten mice by tumor size.

Group 1 received 0.5 ml of phosphate buffered saline solution administered i.p. twice weekly;

Group 2 received anti-DT purified antibodies, 0.25 mg/0.5 ml, i.p. twice weekly;

Group 3 received anti-GnRH purified antibodies 0.35 mg/0.5 ml i.p. twice weekly;

Group 4 received 5 mg of Tamoxifen in a pellet implanted subcutaneously which is sufficient for 60 days;

Group 5 mice received a placebo pellet for 60 days; and

Group 6 mice received 0.72 mg of estradiol (E2) pellet implanted subcutaneously which is sufficient for 60 days.

Mice were evaluated on a twice per week basis regarding tumor progression, and removed from the studies when the tumors reached a size of 200 mm$^2$. The data collected were analyzed as illustrated in FIGS. 6–9.

Figure 6:
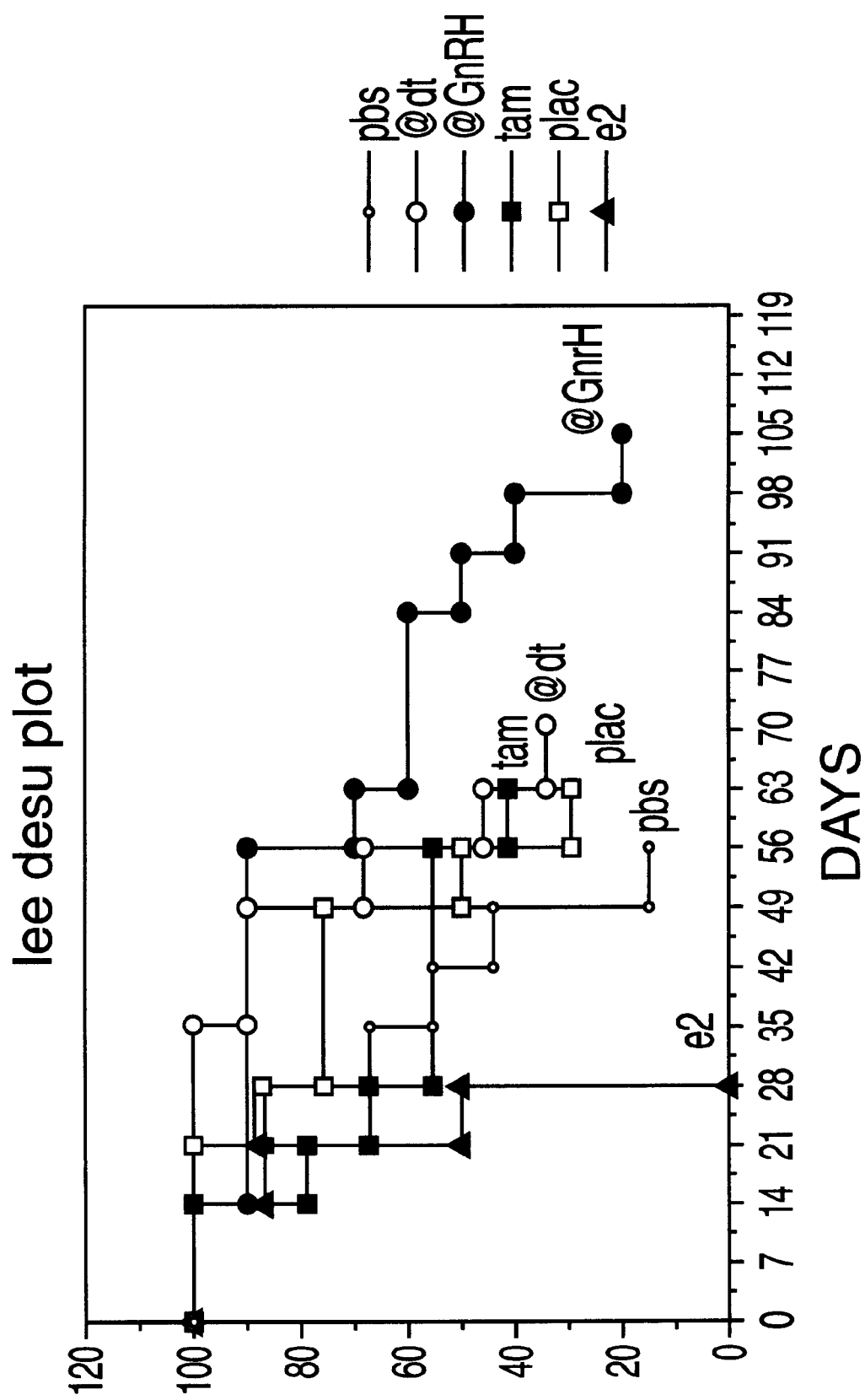
FIG. 6: Depicts a Lee Desu plot showing the percent survival of tumor-bearing nude mice after day of therapy with anti-GnRH antibodies, anti-DT antibodies, Tamoxifen, estradiol (E2), phosphate-buffered saline (PBS) and placebo. The graph shows the percent of mice surviving which have tumor sizes less than 200 $mm^2$.
Figure 7:
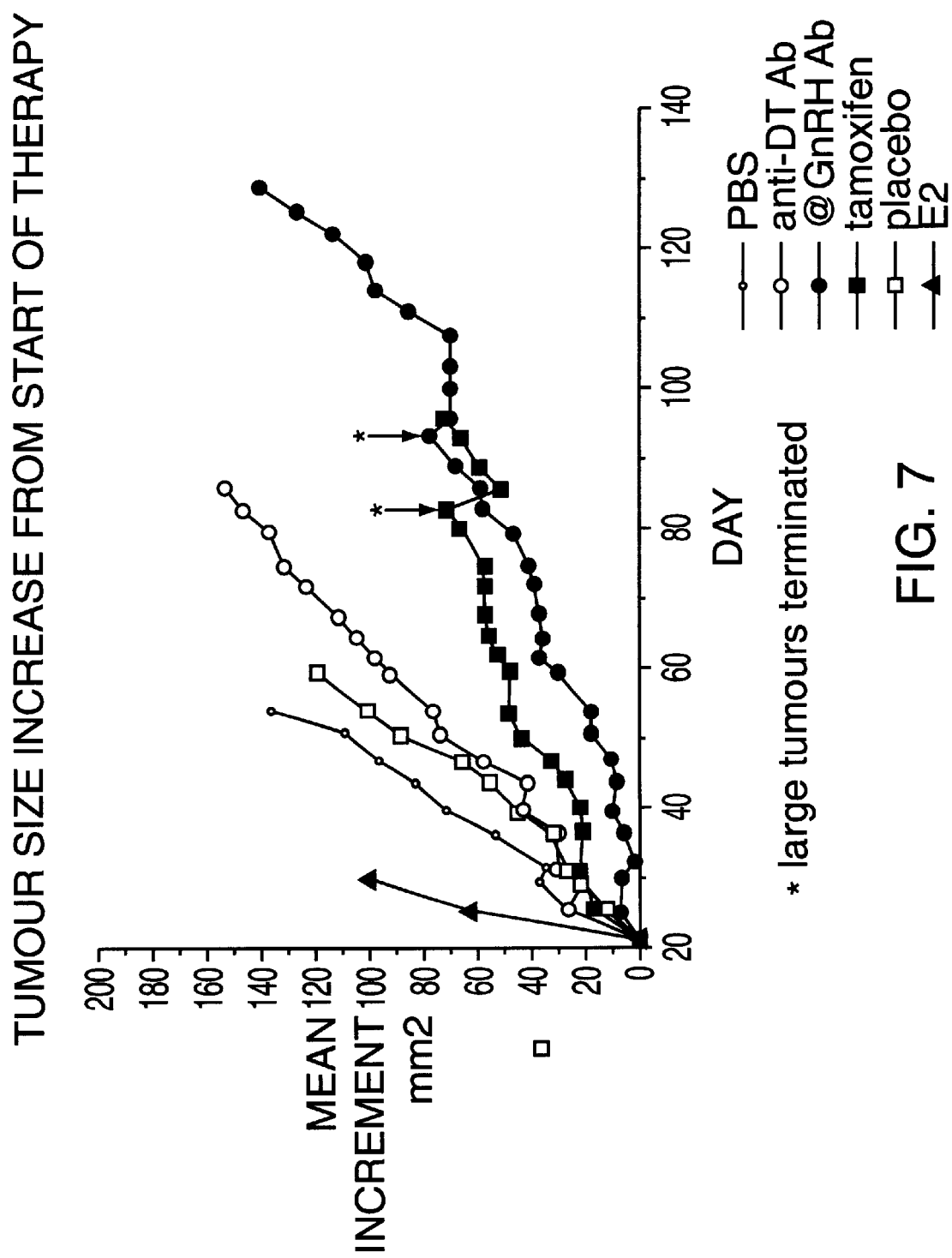
FIG. 7: Shows the increase in tumor size from the start of anti-GnRH and anti-DT antibodies, PBS, Tamoxifen, placebo and E2 control therapies in nude mice with human breast tumor xenografts of the same animals described in FIG. 6.

FIG. 6 is a Lee Desu plot analysis which demonstrates that mice treated with anti-GnRH antibodies have a longer survival time than those of the control therapies. The Lee Desu analysis is a statistical analysis which applies to the survival of the animals under study, as indicated by 100% of the animals surviving at time 0 of the study, since they have not reached a chosen criteria i.e., tumors reaching 200 mm$^2$ or doubling in size. As the tumors in the mice do attain the chosen criteria, they are removed from the study, so the percentage of animals remaining in each group falls. As can be seen in FIG. 6 and Table 10, the median time in days for the tumors to reach 200 mm$^2$ in size are 45.5 days for PBS, 28 days for E2, 61.7 for anti-DT therapy, 58.8 days for Tamoxifen, 56 days for placebo and 91.0 days for anti-GnRH antibody therapy. The Lee Desu survival analysis on this data indicates that E2 treated tumors reach the target size significantly earlier than all groups except Tamoxifen. The PBS treated groups reached the target size significantly earlier than the anti-DT and anti-GnRH treatment groups. Approximately 20% of the mice in this study had tumors less than 200 mm$^2$ at day 105 of GnRH therapy. FIG. 7 shows the effects of the therapies on the size of the tumors over the period that the mice were under study. As can be seen, the anti-GnRH antibody treatment proved effective in slowing tumor growth in this experiment.

EXAMPLE 10

Figure 8A:
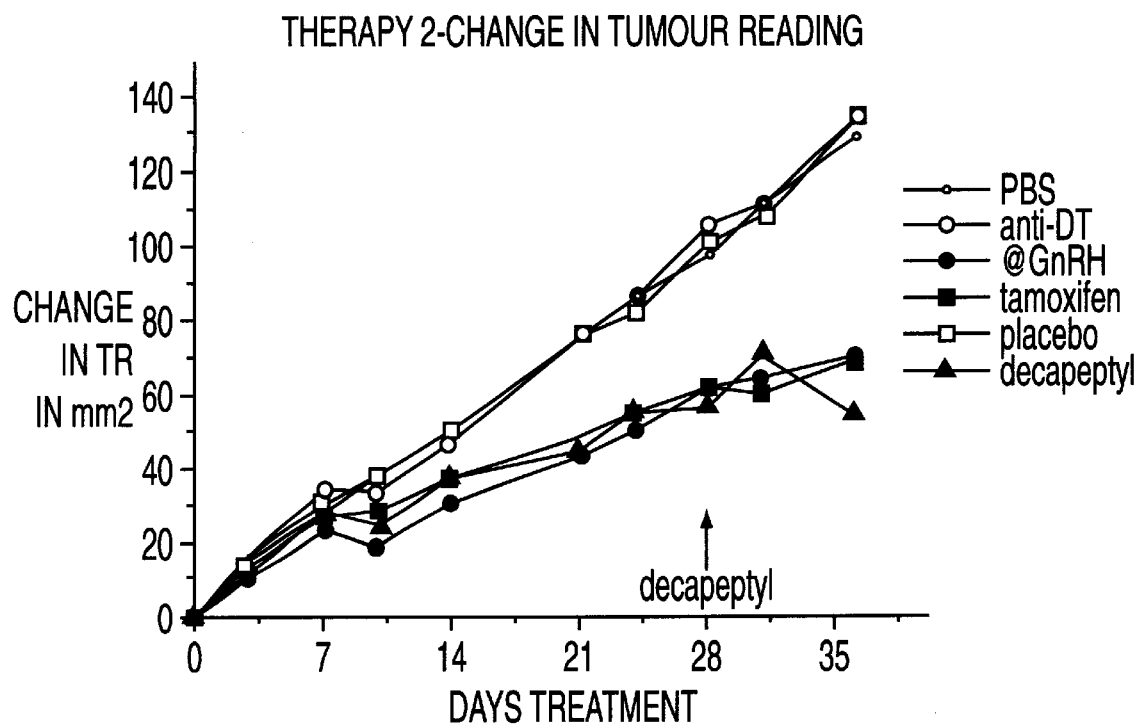
FIG. 8: A. Depicts the change in breast tumor size as measured in $mm^2$, following therapy with anti-GnRH and PBS, anti-DT, Tamoxifen, placebo and decapeptyl control therapies. B. Depicts the mean tumor size as measured in $mm^2$, following therapy with anti-GnRH and Tamoxifen, anti-DT, decapeptyl, placebo and PBS control therapies.
Figure 8B:
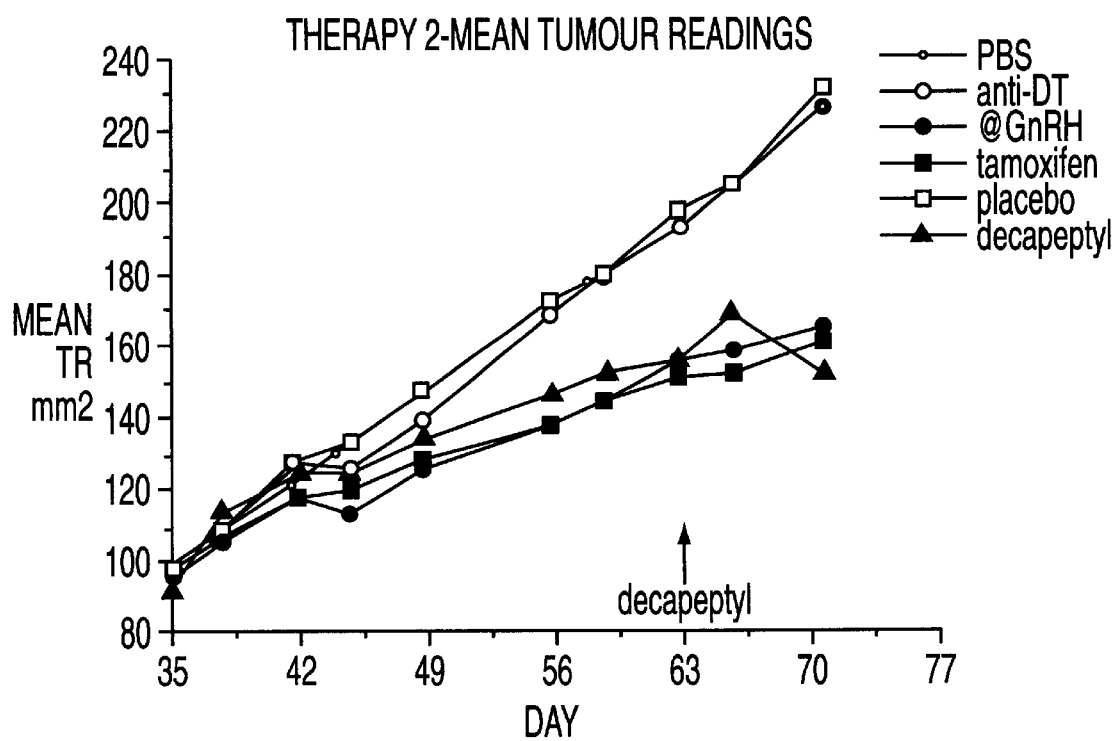
Figure 9A:
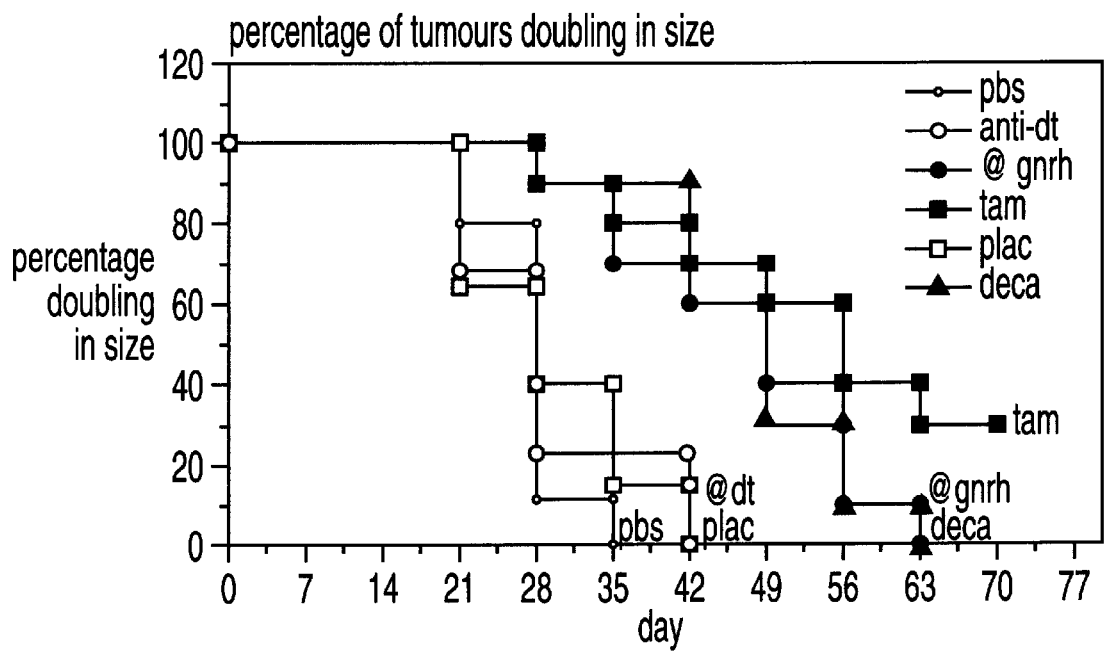
FIG. 9: A. Depicts a Lee Desu plot analysis of data obtained from the same mice as in FIG. 8, showing the percentage of nude mice with implanted breast cancer tumors surviving following therapy with anti-GnRH and Tamoxifen, anti-DT, decapeptyl, placebo and PBS control therapies. B. Depicts a Lee Desu plot of data from same mice as in A, showing the time for tumors to reach 200 $mm^2$ in nude mice following treatment with anti-GnRH and Tamoxifen, anti-DT, decapeptyl, placebo and PBS controls.
Figure 9B:
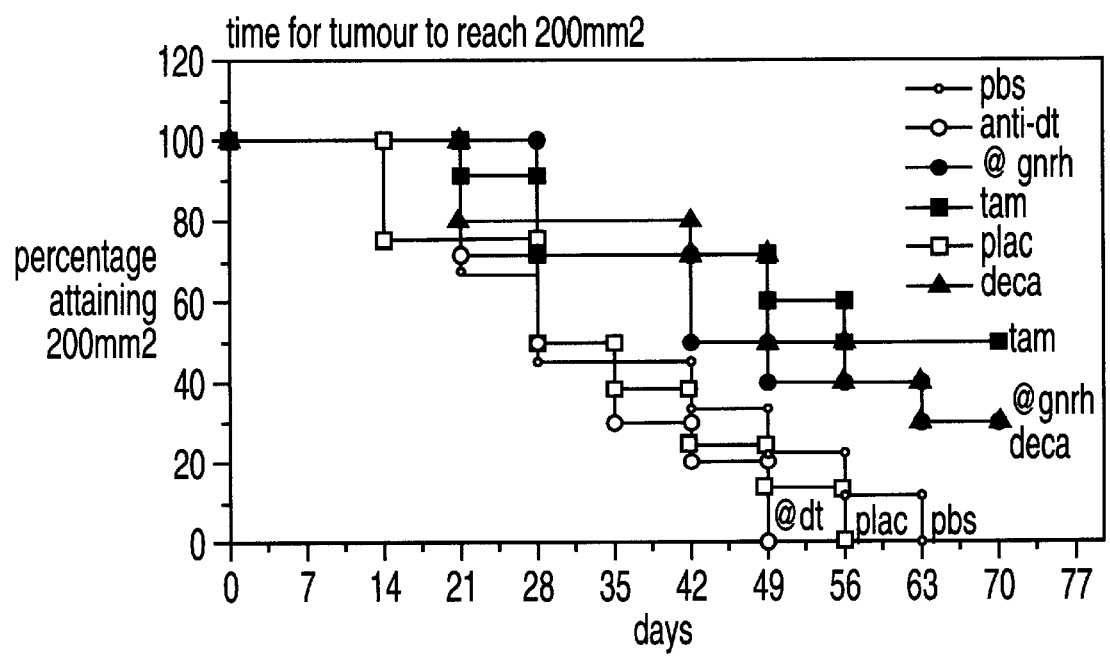

This experiments were performed as described in Example 9 with the exception that mice in group 6 received a subcutaneous injection of decapeptyl which lasts for 28 days, then the injection is repeated every 28 days for the rest of the experiments. In addition, all therapies began at the same time in all mice. The data derived from experiments of this example are illustrated in FIGS. 8 and 9. As can be seen, all three treatments, i.e., anti-GnRH antibodies, Tamoxifen and the LHRH antagonist decapeptyl show similar marked reduction in the rate of tumor growth in comparison with all three control groups, i.e., placebo, PBS and anti-DT antibodies. By day 71, which is equal to the 36 days of therapy, tumors of the anti-GnRH, Tamoxifen and decapeptyl treated animals were significantly smaller than those of the control groups. This is true for both actual tumor size indicated as tumor readings on the graphs , and for change in tumor size which is the difference in growth of the tumor since the start of the therapy. Similarly, as in Example 9, the change in size of the tumor becomes significant at an earlier time point than actual tumor size does, indicating that inhibition of the growth of the tumor is more effective early in the therapy. The treatment groups which include anti-GnRH antibody therapy, Tamoxifen and decapeptyl do not differ from each other significantly for tumor reading or for change in tumor size. Thus, the anti-GnRH antibody therapy appears as good as Tamoxifen or decapeptyl treatment after 36 days of therapy. In addition, by day 113 of the experiment which equals 99 days after treatment, only 6 animals remained with tumors less than 250 mm$^2$, two of which are in the anti-GnRH treated group and four which were given Tamoxifen.

The Lee Desu plot analysis of the data up to day 70 of treatment show the median time for tumors to reach 200 mm$^2$ to be 33 to 35 days for control groups and 49 days for anti-GnRH antibody therapy, in comparison to 56 days for decapeptyl and 70 days for Tamoxifen treatment. Median time for tumors to double in size are 30 to 32 days for controls, 52.5 days for anti-GnRH antibody therapy, 52.5 days for decapeptyl treatment and 59.5 days for treatment with Tamoxifen.

In addition, when mice were killed after tumors reached 200 mm$^2$, the ovaries and uteri were also analyzed. The ovaries and uteri are smaller in anti-GnRH antibody and decapeptyl treated animals than in controls, i.e., PBS, placebo and anti-DT treated indirectly indicating the effectiveness of treatment on reproductive hormone levels, which is smaller in anti-GnRH therapy than in decapeptyl treated groups. Ovaries and uteri from Tamoxifen treated animals examined were heavy and some had clear vacuoles associated with the ovaries.

Tables 10, 11 and 12 below further illustrate statistically analyzed data between pairs of treatment.

TABLE 10

| | Lee Desu | |
|---|---|---|
| | Median time in days for tumor to attain 200 mm$^{22}$ | Median time in days for Tumor to double in Size |
| PBS | 33.3 | 30.9 |
| anti-DT | 35.0 | 30.6 |
| anti-GnRH | 49.0 | 52.5 |
| Tamoxifen | 70+ | 59.5 |
| placebo | 35.0 | 31.5 |
| E2 | 36.0 | 52.5 |

TABLE 10-continued

| | p values for pairwise comparisons of time in days for tumor | |
|---|---|---|
| | to attain 200 mm$^2$ | to double in size |
| anti-GnRH v PBS | 0.058 | 0.0004 |
| anti-GnRH v anti-DT | 0.036 | 0.0016 |
| Tamoxifen v placebo | 0.053 | 0.0018 |
| Decapeptyl v PBS | 0.09 | 0.0003 |
| anti-GnRH v Tamoxifen | 0.64 | 0.27 |
| anti-GnRH v Decapeptyl | 0.85 | 0.76 | comparisons deemed significant if p < 0.05

TABLE 11

Direct comparison between pairs of treatments for change in size of tumor start of treatment.
Table of p values
Mann Whitney-Statistical Analysis of Data
(significant if p < 0.05 in bold)

| Days of Treatment | PBS v anti-DT | PBS v anti-GnRH | Tamoxifen v placebo |
|---|---|---|---|
| 3 | 0.39 | 0.84 | 0.76 |
| 7 | 0.65 | 0.27 | 0.47 |
| 10 | 0.54 | 0.005 | 0.23 |
| 14 | 0.35 | 0.013 | 0.17 |
| 21 | 0.54 | 0.006 | 0.03 |
| 24 | 0.90 | 0.004 | 0.10 |
| 28 | 0.93 | 0.006 | 0.02 |
| 31 | 0.78 | 0.013 | 0.01 |
| 36 | 0.78 | 0.010 | 0.003*(0.045) |

| Days of Treatment | anti-GnRH v anti-DT | anti-GnRH v Tamoxifen | anti-GnRH v Decapeptyl |
|---|---|---|---|
| 3 | 0.33 | 0.57 | 0.91 |
| 7 | 0.09 | 0.62 | 0.68 |
| 10 | 0.06 | 0.14 | 0.12 |
| 14 | 0.05 | 0.57 | 0.43 |
| 21 | 0.01 | 0.68 | 0.60 |
| 24 | 0.006 | 0.60 | 0.57 |
| 28 | 0.004 | 0.88 | 0.60 |
| 31 | 0.005 | 0.79 | 0.62 |
| 36 | 0.001*(0.033) | 0.79 | 0.12 |

| Days of Treatment | PBS v Decapeptyl | Tamoxifen v Decapeptyl |
|---|---|---|
| 3 | 0.49 | 0.63 |
| 7 | 0.84 | 0.51 |
| 10 | 0.07 | 0.73 |
| 14 | 0.05 | 1.00 |
| 21 | 0.016 | 0.91 |
| 24 | 0.013 | 0.97 |
| 28 | 0.005 | 0.71 |
| 31 | 0.022 | 0.33 |
| 36 | 0.001*(0.046) | 0.24 |

*(Mann Whitney/p value) becomes significant for direct Tumor readings as well as for change in size.

The data obtained from the experiments for paired treatment groups were statistically compared by analysis of variance (ANOVA) using repeated measures between day 0 and day 24 of treatment to determine whether the effect of the two treatments over time differed. In these experiments, animals were nested within treatment groups, and the results are shown below.

TABLE 12

|  | ANOVA with nesting | | ANOVA/GLM no nesting | |
|---|---|---|---|---|
|  | A | B | A | B |
| anti-GnRH v Pbs | nd | nd | 0.000* | 0.000 |
| anti-GnRH v anti-DT | 0.005* | 0.09* | 0.000* | 0.000 |
| anti-GnRH v Tamoxifen | 0.70 | 0.88 | 0.32 | 0.71 |
| anti-GnRH v decapeptyl | 0.75* | 0.86 | 0.43 | 0.66 |
| Tamoxifen v placebo | nd | nd | 0.000* | 0.000* |
| PBS v decapeptyl | nd | nd | 0.000* | 0.001* |
| Tamoxifen v decapeptyl | 0.89 | 0.76 | 0.73 | 0.46 |
| PBS v. anti-DT | nd | nd | 0.51 | 0.99 |

*Treatment × time interaction for a pair of treatments (p < 0.05).
(p values significant if <0.05 in bold)
nd = not done because nesting not possible
A Change in size fron start of treatment (on days 3, 7, 10, 14, 21, 24, 28, 31 and 36)
B Direct tumor readings (on days 0, 10, 24, 28, 31 and 36)

The data indicate that the two (PBS, placebo and anti-DT control and anti-GnRH experimental) treatments significantly differ in their effect on tumor growth over time. In most cases, both treatments allow increase in tumor size over time, but at differing rates which is faster in control than treatment groups.

In the case of anti-GnRH v Decapeptyl where the treatments do not differ significantly from each other, it reflects the drop in tumor reading seen following readministration of the decapeptyl at 28 days (see FIG. 9).

The data provided above indicate that anti-gnrh immunogenic therapy would be as effective in the treatment of hormone-dependent breast cancer tumor as tamoxifen which is an existing therapy for the treatment of hormone dependent cancers.

We claim:

1. A method for treatment of gonadotropin hormone-dependent or gonadal steroid hormone-dependent cancer, comprising administering to a mammal in need thereof a therapeutically effective amount of anti-GnRH antibodies which bind and neutralize the hormone GnRH in vivo.

2. A method for the treatment of a gonadotropin or gonadal steroid hormone-dependent disease, comprising administering to a mammal a therapeutically effective amount of an anti-GnRH immunogenic composition comprising a peptide selected from the group consisting of Cys-Pro-Pro-Pro-Pro-Ser-Ser-Glu-His-Trp-Ser-Tyr-Gly-Leu-Arg-Pro-GlyNH$_2$ (SEQ ID No. 5 in the Sequence Listing) pGlu-His-Trp-Ser-Tyr-Gly-Leu-Arg-Pro-Gly-Ser-Ser-Pro-Pro-Pro-Pro-Cys (SEQ ID No: 6 in the Sequence Listing), Cys-Pro-Pro-Pro-Pro-Arg-Glu-His-Trp-Ser-Tyr-Gly-Leu-Arg-Pro-GlyNH$_2$ (SEQ ID No. 7 in the Sequence Listing) and pGlu-His-Trp-Ser-Tyr-Gly-Leu-Arg-Pro-Gly-Arg-Pro-Pro-Pro-Pro-Cys (SEQ ID No. 2 in the Sequence Listing) conjugated through the terminal Cys residue of the spacer peptide to an immunogenic carrier, the peptide to carrier ratio being in the range of 4.7 to 30.1 peptide molecules per carrier molecule.

3. The method of claim 1 or 2 wherein the therapeutically effective amount of anti-GnRH antibodies is tumor growth rate reducing.

4. The method of claim 1 or 2 wherein the hormone dependent-disease cancer is selected from the group consisting of breast cancer, uterine cancer, and prostrate cancer.

5. The method of claim 2, wherein the immunogenic carrier is diphtheria toxoid or tetanus toxoid.

6. The method of claim 2, wherein the hormone-dependent disease is a breast cancer.

7. A method of claim 1 or 2 wherein the hormone-dependent disease is prostatic cancer.

8. A method for the treatment of gonadotropin hormone-dependent disorder or disease comprising administering to a mammal in need thereof of a therapeutically effective amount of anti-GnRH immunogenic conjugate effective for neutralizing GnRH so as to reduce GnRH activity in vivo.

9. The method of claim 8 wherein the disease comprises estrogen dependent-cancer.

10. The method for claim 8 wherein the disorder comprises endometriosis or prostatic hypertrophy.

* * * * *